US012758188B2

(12) United States Patent
Kim et al.

(10) Patent No.: US 12,758,188 B2
(45) Date of Patent: Oct. 13, 2026

(54) TRANSPARENT-ULTRASONIC-SENSOR-BASED OPTICAL-ULTRASONIC INTEGRATED ENDOSCOPIC PROBE, ENDOSCOPE APPARATUS, AND CATHETER APPARATUS

(71) Applicants: POSCO CO., LTD, Pohang-si (KR); POSTECH Research and Business Development Foundation, Pohang-si (KR)

(72) Inventors: Chul-Hong Kim, Pohang-si (KR); Hyung-Ham Kim, Pohang-si (KR); Jeong-Woo Park, Daegu (KR); Seong-Hee Cho, Busan (KR); Jae-Woo Kim, Pohang-si (KR); Da-Som Heo, Incheon (KR); Byul-Lee Park, Pohang-si (KR)

(73) Assignees: POSCO CO., LTD, Pohang-si (KR); POSTECH Research and Business Development Foundation, Pohang-si (KR)

( * ) Notice: Subject to any disclaimer, the term of this patent is extended or adjusted under 35 U.S.C. 154(b) by 0 days.

(21) Appl. No.: 18/284,462

(22) PCT Filed: Oct. 18, 2021

(86) PCT No.: PCT/KR2021/014448
§ 371 (c)(1),
(2) Date: Sep. 27, 2023

(87) PCT Pub. No.: WO2022/220350
PCT Pub. Date: Oct. 20, 2022

(65) Prior Publication Data

US 2024/0164752 A1 May 23, 2024

(30) Foreign Application Priority Data

Apr. 13, 2021 (KR) ........................ 10-2021-0047702

(51) Int. Cl.
*A61B 8/00* (2006.01)
*A61B 1/00* (2006.01)
(Continued)

(52) U.S. Cl.
CPC ........ *A61B 8/4461* (2013.01); *A61B 1/00091* (2013.01); *A61B 1/00094* (2013.01);
(Continued)

(58) Field of Classification Search
CPC ..... A61B 5/6852; A61B 8/4416; A61B 8/445; A61B 8/4483; A61B 1/00091; A61B 1/00094
See application file for complete search history.

(56) References Cited

U.S. PATENT DOCUMENTS 6,238,386 B1 * 5/2001 Muller ............. A61B 17/00234 600/407
6,979,292 B2 12/2005 Kanayaa et al.
(Continued)

FOREIGN PATENT DOCUMENTS

CN 104349705 A 2/2015
CN 108472054 A 8/2018
(Continued)

OTHER PUBLICATIONS

Communication dated Jul. 6, 2024 issued by the Korean Patent Office in application No. 10-2021-0047702.
(Continued)

*Primary Examiner* — Oommen Jacob
(74) *Attorney, Agent, or Firm* — Sughrue Mion, PLLC

(57) ABSTRACT

A transparent-ultrasonic-sensor-based optical-ultrasonic integrated endoscopic probe according to one embodiment of the present disclosure may comprise: an optical fiber laser unit for emitting light; a transparent ultrasonic sensor, which is arranged between an object to be measured and the optical
(Continued)

fiber laser unit to transmit, therethrough, the light emitted from the optical fiber laser unit, coaxially aligned with the light emitted from the optical fiber laser unit, radiating ultrasonic waves at the object, and receiving reflected ultrasonic waves; and a camera for acquiring an image of the object through the transparent ultrasonic sensor.

7 Claims, 18 Drawing Sheets

(51) Int. Cl.
*A61B 1/05* (2006.01)
*A61B 1/07* (2006.01)
*A61B 8/12* (2006.01)

(52) U.S. Cl.
CPC .................. *A61B 1/05* (2013.01); *A61B 1/07* (2013.01); *A61B 8/12* (2013.01)

(56) References Cited

U.S. PATENT DOCUMENTS

| | | | | |
|---|---|---|---|---|
| 8,353,830 | B2 | 1/2013 | Kanayama et al. | |
| 8,454,512 | B2 * | 6/2013 | Wang | G01N 29/0681 600/459 |
| 8,784,321 | B2 | 7/2014 | Courtney et al. | |
| 9,631,971 | B2 | 4/2017 | Oh et al. | |
| 2003/0208209 | A1 | 11/2003 | Gambale et al. | |
| 2006/0184042 | A1 * | 8/2006 | Wang | A61B 5/0073 600/476 |
| 2008/0045865 | A1 * | 2/2008 | Kislev | A61B 5/411 601/3 |
| 2008/0154136 | A1 | 6/2008 | Webler | |
| 2011/0201914 | A1 * | 8/2011 | Wang | A61B 5/0059 600/407 |
| 2012/0165669 | A1 | 6/2012 | Barley et al. | |
| 2013/0096413 | A1 * | 4/2013 | Ashkenazi | G01N 29/0654 600/407 |
| 2015/0051485 | A1 | 2/2015 | Itoh et al. | |
| 2015/0065798 | A1 | 3/2015 | Kuroda | |
| 2015/0173626 | A1 * | 6/2015 | Irisawa | G01N 21/1702 600/407 |
| 2016/0095577 | A1 | 4/2016 | Itoh et al. | |
| 2018/0228464 | A1 | 8/2018 | Yang et al. | |
| 2019/0076119 | A1 * | 3/2019 | Yang | A61B 1/07 |
| 2019/0261947 | A1 | 8/2019 | Themelis | |
| 2020/0100655 | A1 * | 4/2020 | Morishima | A61B 1/053 |
| 2020/0246041 | A1 | 8/2020 | Morimoto et al. | |
| 2020/0289088 | A1 | 9/2020 | Kim et al. | |
| 2021/0145265 | A1 * | 5/2021 | Morishima | A61B 1/053 |
| 2022/0133273 | A1 * | 5/2022 | Dangi | A61B 5/0095 600/459 |
| 2022/0334086 | A1 | 10/2022 | Kim et al. | |
| 2023/0204492 | A1 | 6/2023 | Kim et al. | |

FOREIGN PATENT DOCUMENTS

| | | | | |
|---|---|---|---|---|
| CN | 108703744 | A | 10/2018 | |
| JP | 60-88531 | A | 5/1960 | |
| JP | 57-180948 | A | 11/1982 | |
| JP | 62-43617 | A | 2/1987 | |
| JP | 7-31617 | A | 2/1995 | |
| JP | 9-135833 | A | 5/1997 | |
| JP | 11151245 | A | 6/1999 | |
| JP | 2004-147940 | A | 5/2004 | |
| JP | 2005-218684 | A | 8/2005 | |
| JP | 2005-224399 | A | 8/2005 | |
| JP | 2011-512994 | A | 4/2011 | |
| JP | 2011-519281 | A | 7/2011 | |
| JP | 2013-504398 | A | 2/2013 | |
| JP | 2014-532520 | A | 12/2014 | |
| JP | 2015-8995 | A | 1/2015 | |
| JP | 2019-146967 | A | 9/2019 | |
| JP | 2019-216951 | A | 12/2019 | |
| KR | 100805463 | B1 | 2/2008 | |
| KR | 10-2013-0045550 | A | 5/2013 | |
| KR | 20140059466 | A * | 5/2014 | A61B 8/08 |
| KR | 10-2015-0035850 | A | 4/2015 | |
| KR | 101638730 | B1 | 7/2016 | |
| KR | 10-2017-0005526 | A | 1/2017 | |
| KR | 10-2018-0094425 | A | 8/2018 | |
| KR | 10-2019-0028955 | A | 3/2019 | |
| KR | 10-2019-0031834 | A | 3/2019 | |
| KR | 10-2020-0132084 | A | 11/2020 | |
| KR | 10-2021-0034466 | A | 3/2021 | |
| KR | 10-2022-0029003 | A | 3/2022 | |
| WO | 2004/042382 | A1 | 5/2004 | |
| WO | 2009/055705 | A2 | 4/2009 | |
| WO | 2012/096778 | A1 | 7/2012 | |
| WO | 2013/067304 | A1 | 5/2013 | |
| WO | 2013/145635 | A1 | 10/2013 | |
| WO | 2015/0051485 | A1 | 2/2015 | |

OTHER PUBLICATIONS

Communication dated Sep. 2, 2024 issued by the European Patent Office in application No. 21937084.8.
Communication dated Sep. 3, 2024 issued by the Japanese Patent Office in application No. 2023-559781.
Jeongwoo Park, et al., "Quadruple Fusion Imaging via Transparent Ultrasound Transducer: Ultrasound, Photoacoustic, Optical Coherence, and Fluorescence Imaging", Proceedings of the National Academy of Sciences, 2021; 118 (11).
Jeongwoo Park, et al., Seamlessly Integrated Optical and Acoustical Imaging Systems Through Transparent Ultrasonic Transducer, Photons Plus Ultrasound: Imaging and Sensing 2020, vol. 11240, p. 112401P.
International Search Report for PCT/KR2021/014448 dated Jul. 18, 2022.
Written Opinion for PCT/KR2021/014448 dated Jul. 18, 2022.
Communication dated Apr. 18, 2026, issued in Chinese Application No. 202180096930.X.

* cited by examiner

TRANSPARENT-ULTRASONIC-SENSOR-BASED OPTICAL-ULTRASONIC INTEGRATED ENDOSCOPIC PROBE, ENDOSCOPE APPARATUS, AND CATHETER APPARATUS

CROSS REFERENCE TO RELATED APPLICATIONS

This application is a National Stage of International Application No. PCT/KR2021/014448 filed Oct. 18, 2021, claiming priority based on Korean Patent Application No. 10-2021-0047702 filed Apr. 13, 2021, the entire disclosures of which are incorporated herein by reference.

TECHNICAL FIELD

The present disclosure relates to a transparent-ultrasonic-sensor-based optical-ultrasonic integrated endoscopic probe, endoscope apparatus, and catheter apparatus.

BACKGROUND ART

An ultrasonic sensor or a transducer is a sensor that enables physical distance measurement from an object and image acquisition of the object based on the principle of converting electrical energy into acoustic energy using characteristics of a piezoelectric material, transferring the acoustic energy to a targeted object, and then converting the reflected acoustic energy back into an electric signal.

Recently, a technology of integrating an optical device such as an optical camera and a laser with an ultrasonic sensor is being actively developed for high-precision sensing operation, high-resolution imaging, and user convenience.

In particular, since there is an advantage of improving accuracy in medical diagnosis, research has been conducted into integrating a conventional ultrasonic imaging system and an optical imaging system, integrating an ultrasonic imaging system and an optical coherence tomography imaging system, integrating an ultrasonic imaging system and a fluorescence imaging system, or the like.

However, since the conventional ultrasonic sensor is opaque, the ultrasonic sensor may not be integrated with an optical device requiring a transparent medium, and may not be arranged on the same axis as the irradiated laser.

This off-axis arrangement is disadvantageous in taking images for various reasons. For example, problems such as misalignment of the system, an increase in complexity, an increase in a system size, and a decrease in a signal-to-noise ratio (SNR) have occurred.

In order to solve the problem of this opaque ultrasonic sensor, U.S. Pat. No. 8,784,321 discloses that a portion of an end surface of the opaque ultrasonic sensor is perforated to form an optical path so that the optical path and the ultrasonic path are arranged on the same axis. However, even in this case, since light may transmit only a portion of the end surface of the ultrasonic sensor, the problem due to the light non-transmittance of the ultrasonic sensor may not be sufficiently solved.

Meanwhile, the present inventors have presented Korean Patent Application No. 10-2020-0039208 ("transparent ultrasonic sensor and method for manufacturing the same") that discloses a lithium niobate (LNO)-based single crystal transparent ultrasonic sensor structure and Korean Patent Application No. 10-2020-0110777 ("ultrasonic-optical multi imaging system based on transparent ultrasonic sensor") that discloses an ultrasonic-optical multi imaging system using a transparent ultrasonic sensor.

(Patent Document 1) U.S. Pat. Publication No. 8,784,321

(Patent Document 2) Korean Patent Application No. 10-2020-0039208

(Patent Document 3) Korean Patent Application No. 10-2020-0110777

DISCLOSURE

Technical Problem

The present disclosure provides a transparent-ultrasonic-sensor-based optical-ultrasonic integrated endoscopic probe, endoscope apparatus, and catheter apparatus capable of improving SNR and miniaturizing a device by utilizing a transparent ultrasonic sensor that enables coaxialization of an ultrasonic path and an optical path.

Technical Solution

In an aspect of the present invention, a transparent-ultrasonic-sensor-based optical-ultrasonic integrated endoscopic probe may include: an optical fiber laser unit emitting light; a transparent ultrasonic sensor arranged between an object to be measured and the optical fiber laser unit to transmit, therethrough, the light emitted from the optical fiber laser unit, coaxially aligned with the light emitted from the optical fiber laser unit, radiating ultrasonic waves at the object, and receiving reflected ultrasonic waves; and a camera acquiring an image of the object through the transparent ultrasonic sensor. In another aspect of the present invention, a transparent-ultrasonic-sensor-based optical-ultrasonic integrated endoscope apparatus may include: the probe; a scanning unit connected to the probe by a cable to control a scanning operation of the probe; and a front-end unit providing light output to the probe through the cable and signal-processing an image acquired by the probe. In another aspect of the present invention, a transparent-ultrasonic-sensor-based optical-ultrasonic integrated catheter apparatus may include: a catheter inserted into a previously set object; a scanning unit connected to the catheter by the cable to control a scanning operation of the catheter; and a front-end unit providing an optical output to the catheter through the cable and signal-processing an image acquired by the catheter, in which the catheter may include an optical fiber laser unit emitting light from the front-end unit and a transparent ultrasonic sensor arranged between an object to be measured and the optical fiber laser unit to transmit, therethrough, the light emitted from the optical fiber laser unit, coaxially aligned with the light emitted from the optical fiber laser unit, radiating ultrasonic waves at the object, and receiving reflected ultrasonic waves and transferring the received reflected ultrasonic waves to the front-end unit.

Advantageous Effects

According to an embodiment of the present disclosure, it is possible to improve SNR and miniaturize a probe or a catheter by using the transparent ultrasonic sensor that enables coaxialization of an ultrasonic path and an optical path.

BEST MODE

Hereinafter, embodiments will be described in detail with reference to the accompanying drawings so that they can be easily practiced by those skilled in the art to which the present disclosure pertains.

Figure 1:
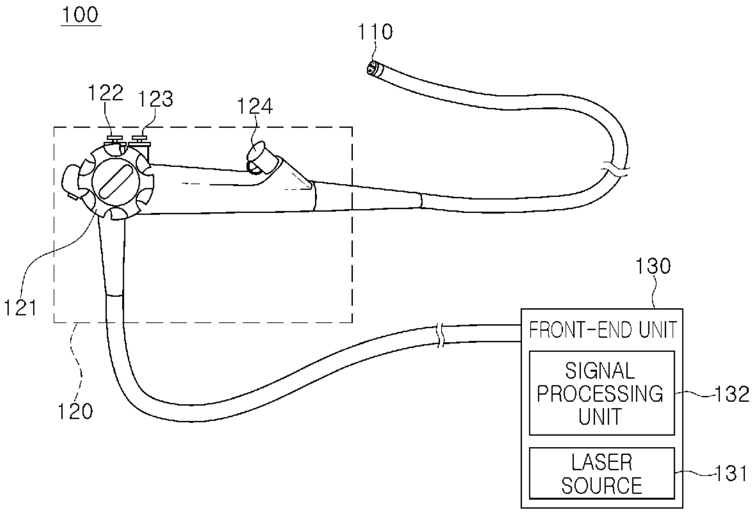
FIG. 1 is a schematic configuration diagram of a transparent-ultrasonic-sensor-based optical-ultrasonic integrated endoscope apparatus or catheter apparatus according to an embodiment of the present disclosure.

FIG. 1 is a schematic configuration diagram of a transparent-ultrasonic-sensor-based optical-ultrasonic integrated endoscope apparatus or catheter apparatus according to an embodiment of the present disclosure.

Referring to FIG. 1, a transparent-ultrasonic-sensor-based optical-ultrasonic integrated endoscope apparatus or catheter apparatus 100 according to an embodiment of the present disclosure may include an endoscopic probe or catheter 110, a manipulation unit 120, and a front-end unit 130.

The endoscopic probe or catheter 110 may be inserted into a previously set object to acquire an ultrasonic image, photoacoustic image, or the like of an object to be captured. As described above, the endoscopic probe or catheter 110 may be inserted into the previously set object to acquire the ultrasonic image, the photoacoustic image, or the like of the object to be captured. For example, in the case of the endoscopic probe inserted into organs such as a stomach and a large intestine of a body, an outer diameter of the endoscopic probe may be about 5 to 15 mm, and in the case of the catheter inserted into a narrow place such as a cardiovascular, a microvessel, and the like, an outer diameter of the catheter may be about 0.5 to 1 mm.

The manipulation unit 120 may control the movement of the endoscopic probe or the catheter 110 connected through a cable. The manipulation unit 120 may include a knob unit 121, a suction valve 122, an air/water valve 123, and an instrument port 124.

The knob unit 121 may control the movement of the endoscopic probe or catheter 110 according to the user's manipulation, the suction valve 122 may control the suction operation of the suction unit installed in the endoscopic probe or catheter 110 to be described later, the air/water valve 123 may control an operation of a water nozzle device installed in the endoscopic probe or catheter 110 to be described later, and the instrument port 124 may control an operation of a medical device through a forceps hole installed in an endoscopic probe or catheter 110 to be described later.

The front-end unit 130 may include a signal processing unit 132 that transmits an ultrasonic signal to the endoscopic probe or catheter 110 through a laser source 131 providing a laser through an optical fiber cable and a signal line, receives and signal-processes the reflected ultrasonic signal, and signal-processes and displays the acquired photoacoustic image or the like.

Figure 2:
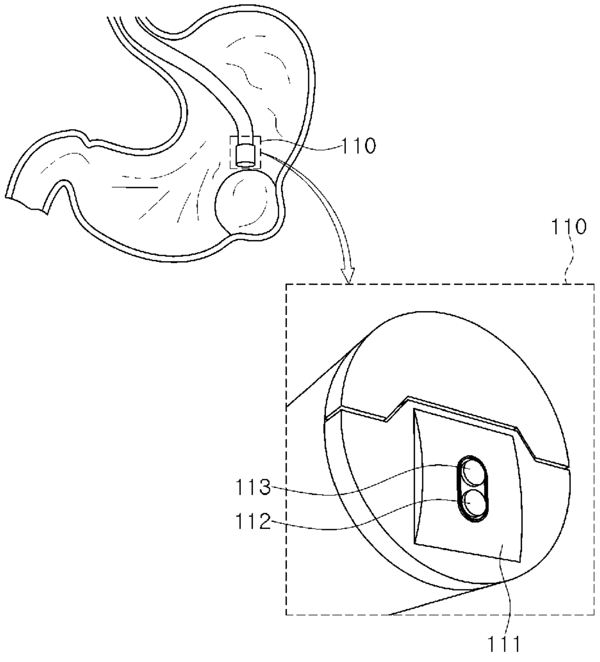
FIG. 2 is a schematic front perspective view of a transparent-ultrasonic-sensor-based optical-ultrasonic integrated endoscopic probe according to an embodiment of the present disclosure.

FIG. 2 is a schematic front perspective view of a transparent-ultrasonic-sensor-based optical-ultrasonic integrated endoscopic probe according to an embodiment of the present disclosure.

Referring to FIG. 2 together with FIG. 1, the transparent-ultrasonic-sensor-based optical-ultrasonic integrated endoscopic probe 110 according to the embodiment of the present disclosure includes an ultrasonic sensor 111, an optical fiber laser unit 112, and a camera 113.

The optical fiber laser unit 112 may receive the laser from the laser source 131 of the front-end unit 130 and emit light to the outside of the probe 110. The optical fiber laser unit 112 may be a laser device of various wavelengths for photoacoustic, OCT, near infra fluorescence (NIRF), near infra spectroscopy (NIRS), and fluorescence imaging. In addition to the laser, the optical fiber laser unit 112 may be a small camera (CCD, CMOS sensor), LED, etc. Although only one optical fiber laser unit 112 is shown, the plurality of optical fiber laser units 112 may be arranged within a limited size to simultaneously acquire a plurality of optical images.

The transparent ultrasonic sensor 111 may be arranged between an object to be measured and the optical fiber laser unit 112 and coaxially aligned with the light emitted from the optical fiber laser unit 112, may transmit the light emitted from the optical fiber laser unit 112, connected to the signal processing unit 132 of the front-end unit 130 through the signal line to radiate ultrasonic waves to the object, and receive reflected ultrasonic waves to acquire an ultrasonic image. The camera 113 may be connected to the signal processing unit 132 of the front-end unit 130 through the signal line to acquire an image of an object through the transparent ultrasonic sensor 111, and may transfer the acquired image to the signal processing unit 132.

As described above, the transparent-ultrasonic-sensor-based optical-ultrasonic integrated endoscopic probe 110 according to the embodiment of the present disclosure transmits the light from the optical fiber laser unit 112 to a rear surface of the transparent ultrasonic sensor 111 to acquire optical/ultrasonic images or signals at the same location as light and ultrasonic waves, reduce a volume of the device and increase the number of forceps holes in an extra portion of the device to add various surgical tools or the like, and overcome a positional inconsistency problem between the conventional ultrasonic and optical images because the ultrasonic/optical may share exactly the same positional information.

FIGS. 3A through 3D are schematic front perspective views of the transparent-ultrasonic-sensor-based optical-ultrasonic integrated endoscopic probe according to the embodiment of the present disclosure.

Referring to FIGS. 3A through 3D together with FIG. 2, the transparent-ultrasonic-sensor-based optical-ultrasonic integrated endoscopic probe 110 according to various embodiments of the present disclosure may further include a suction unit 114 that sucks a previously set substance, a forceps hole 115, and a water nozzle device 116 that ejects water. As described above, by increasing the number of forceps holes in the extra portion of the device due to the reduced volume of the device, the plurality of forceps holes 115 performing pre-set medical functions such as incision and suture may be provided.

Figure 3A:
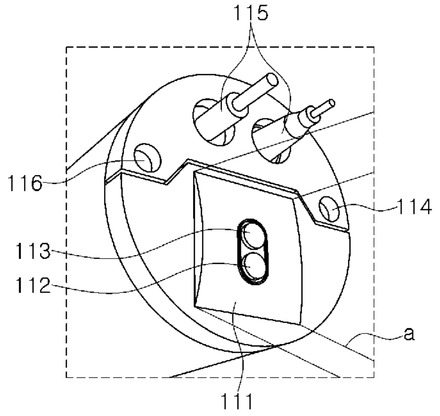
FIGS. 3A through 3D are schematic front perspective views of the transparent-ultrasonic-sensor-based optical-ultrasonic integrated endoscopic probe according to various embodiments of the present disclosure.
Figure 3B:
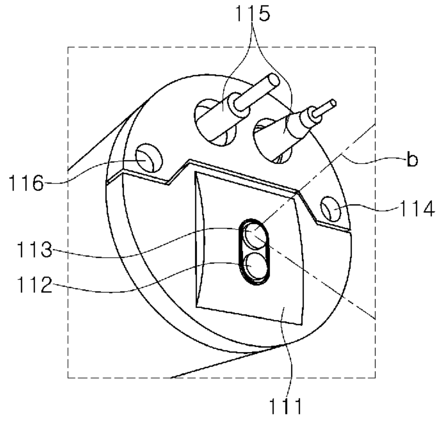
Figure 3C:
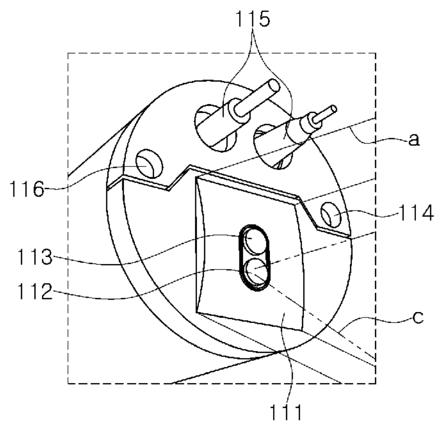
Figure 3D:
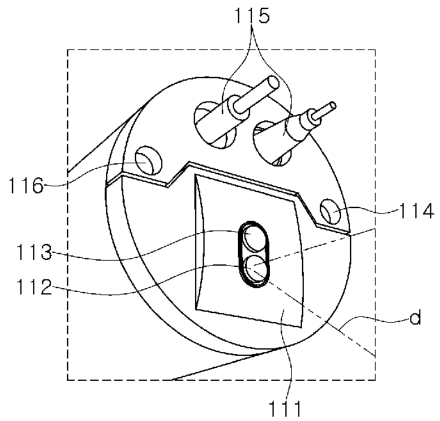

First, the transparent-ultrasonic-sensor-based optical-ultrasonic integrated endoscopic probe 110 according to various embodiments of the present disclosure may acquire, referring to FIG. 3A, an ultrasonic image a of an object through the transparent ultrasonic sensor 111, acquire, referring to FIG. 3B, an image b of an object through the camera 113, acquire, referring to FIG. 3C, photoacoustic images a and c using the optical fiber laser unit 112 and the transparent ultrasonic sensor 111, and acquire, referring to FIG. 3D, a fluorescence image d using the optical fiber laser unit 112 alone.

Meanwhile, except for the configuration in which the camera is excluded from the endoscopic probe described above, the operation and configuration of the catheter employed in the transparent-ultrasonic-sensor-based optical-ultrasonic integrated catheter apparatus 100 according to an embodiment of the present disclosure are similar to those of the endoscopic probe, and therefore, a detailed description thereof will be omitted.

The transparent-ultrasonic-sensor-based optical-ultrasonic integrated endoscopic probe or catheter 110 according to various embodiments of the present disclosure may be a front viewing type or a side viewing type.

In the transparent-ultrasonic-sensor-based optical-ultrasonic integrated endoscopic probe or catheter 110 illustrated in the drawings to be described later, the transparent ultrasonic sensor may focus or radiate ultrasonic signals.

Figure 4A:
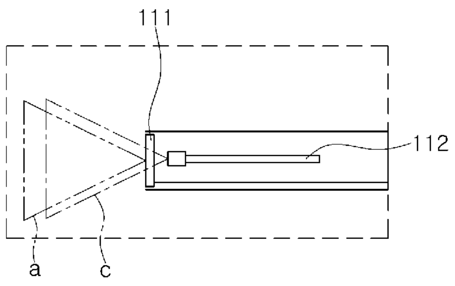
FIGS. 4A through 4C are schematic configuration diagrams of a front viewing type transparent-ultrasonic-sensor-based optical-ultrasonic integrated endoscopic probe or catheter according to various embodiments of the present disclosure.
Figure 4B:
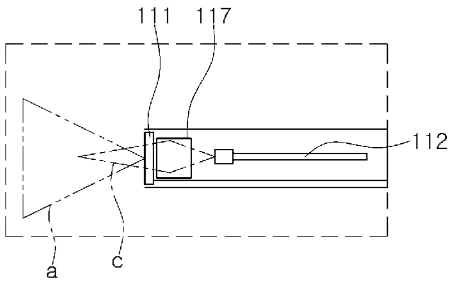
Figure 4C:
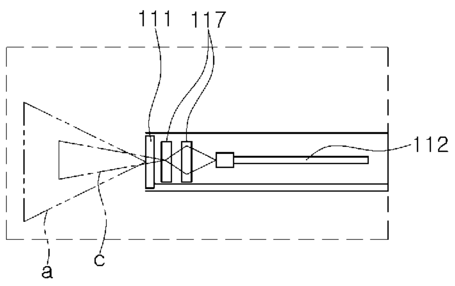

FIGS. 4A through 4C are schematic configuration diagrams of a front viewing type transparent-ultrasonic-sensor-based optical-ultrasonic integrated endoscopic probe or catheter according to various embodiments of the present disclosure.

Referring to FIG. 4A, in the transparent-ultrasonic-sensor-based optical-ultrasonic integrated endoscopic probe or catheter 110 according to various embodiments of the present disclosure, the optical fiber laser unit 112 may be located on the rear surface of the transparent ultrasonic sensor 111, which transmits/receives ultrasonic waves a from an end to a front, to emit light c through the transparent ultrasonic sensor 111.

Referring to FIG. 4B, in the transparent-ultrasonic-sensor-based optical-ultrasonic integrated endoscopic probe or catheter 110 according to various embodiments of the present disclosure, an optical lens 117 may be arranged between the transparent ultrasonic sensor 111 and the optical fiber laser unit 112 to focus light c from the optical fiber laser unit 112. The optical lens 117 may be various such as a GRIN lens, a ball lens, and a convex lens.

Referring to FIG. 4C, in the transparent-ultrasonic-sensor-based optical-ultrasonic integrated endoscopic probe or catheter 110 according to various embodiments of the present disclosure, a plurality of optical lenses 117 may be arranged between the transparent ultrasonic sensor 111 and the optical fiber laser unit 112 to adjust an angle or distance where the light c from the optical fiber laser unit 112 spreads. The optical lens 117 at this time may correspond to any lens, diffuser, or the like that may spread light.

Meanwhile, the transparent-ultrasonic-sensor-based optical-ultrasonic integrated endoscopic probe or catheter 110 according to various embodiments of the present disclosure may further include a reflector.

Figure 5A:
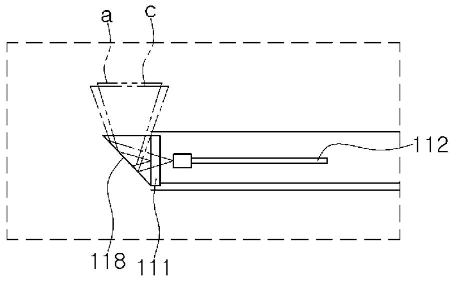
FIGS. 5A through 5C are schematic configuration diagrams of a transparent-ultrasonic-sensor-based optical-ultrasonic integrated endoscopic probe or catheter in which a reflector is added to the front viewing type probe or catheter according to various embodiments of the present disclosure.
Figure 5B:
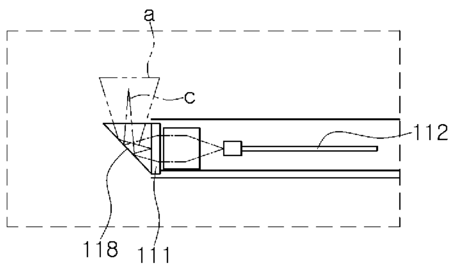
Figure 5C:
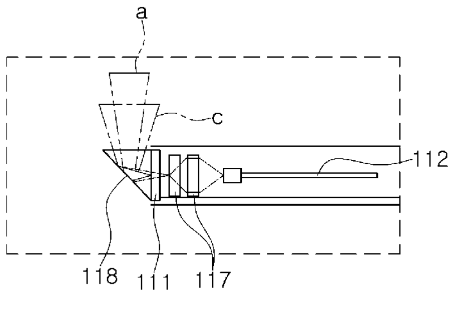
Figure 6A:
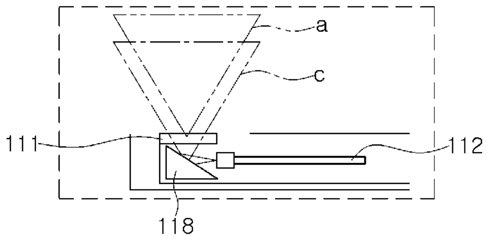
FIGS. 6A through 6I are schematic configuration diagrams of a transparent-ultrasonic-sensor-based optical-ultrasonic integrated endoscopic probe or catheter in which a reflector is added to a side viewing type probe or catheter according to various embodiments of the present disclosure.
Figure 6B:
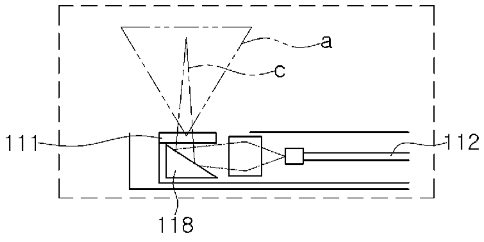
Figure 6C:
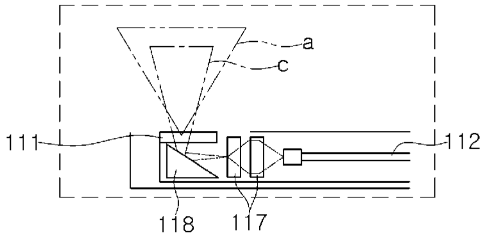
Figure 6D:
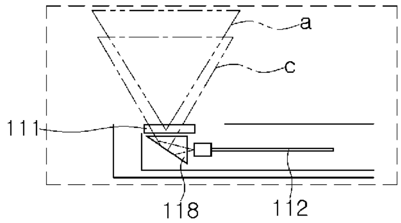
Figure 6E:
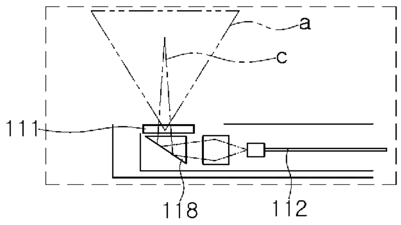
Figure 6F:
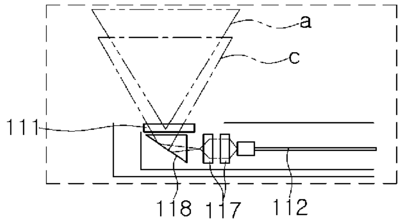
Figure 6G:
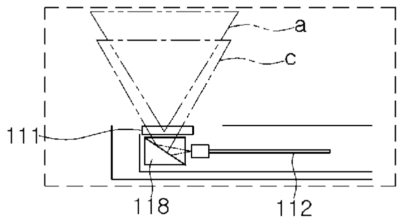
Figure 6H:
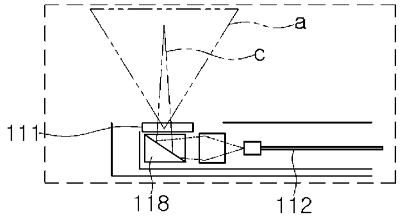
Figure 6I:
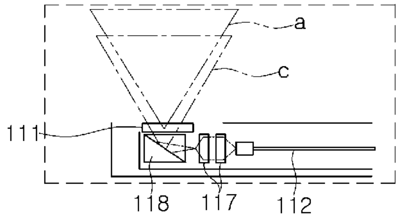
Figure 7A:
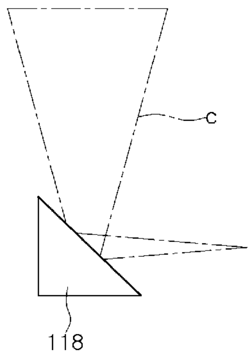
FIGS. 7A through 7D each are diagrams illustrating an embodiment of a reflector employed in a transparent-ultrasonic-sensor-based optical-ultrasonic integrated endoscope apparatus or catheter apparatus according to an embodiment of the present disclosure.
Figure 7B:
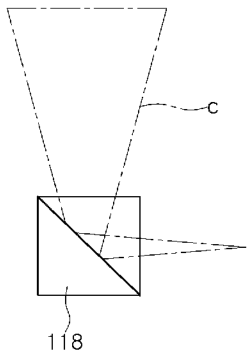
Figure 7C:
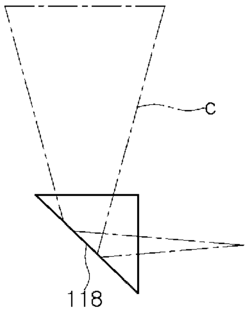
Figure 7D:
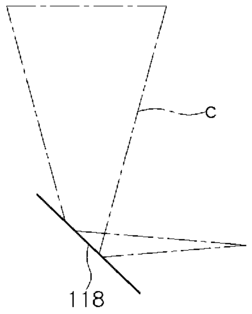

FIGS. 5A through 5C are schematic configuration diagrams of a transparent-ultrasonic-sensor-based optical-ultrasonic integrated endoscopic probe or catheter in which a reflector is added to the front viewing type probe or catheter according to various embodiments of the present disclosure.

Referring to FIGS. 5A through 5C, the front viewing type transparent-ultrasonic-sensor-based optical-ultrasonic integrated endoscopic probe or catheter 110 according to various embodiments of the present disclosure may further include a reflector 118 to transmit/receive ultrasonic waves to a side surface of the transparent-ultrasonic-sensor-based optical-ultrasonic integrated endoscopic probe or catheter 110 and emit light. Similarly, when a camera (not illustrated) is included, an image of an object may be acquired. The reflector 118 may be arranged in front of the transparent ultrasonic sensor 111 to change an angle between the ultrasonic wave of the transparent ultrasonic sensor 111 and the light from the optical fiber laser unit 112.

FIGS. 6A through 6I are schematic configuration diagrams of a transparent-ultrasonic-sensor-based optical-ultrasonic integrated endoscopic probe or catheter in which a reflector is added to a side viewing type probe or catheter according to various embodiments of the present disclosure.

Referring to FIGS. 6A through 6I, the side viewing type transparent-ultrasonic-sensor-based optical-ultrasonic integrated endoscopic probe or catheter 110 according to various embodiments of the present disclosure may include the optical fiber laser unit 112 that is located on the rear surface of the transparent ultrasonic sensor 111 transmitting/receiving ultrasonic waves a to emit light c through the transparent ultrasonic sensor 111, and the reflector 118 that is arranged between the transparent ultrasonic sensor 111 and the optical fiber laser unit 112 to change an angle of light from the optical fiber laser unit 112. In addition, the optical lens 117 may be arranged between the reflector 118 and the optical fiber laser unit 112 to focus the light c from the optical fiber laser unit 112, or the plurality of optical lenses 117 may be arranged to adjust the angle and distance at which the light c spreads from the optical fiber laser unit 112.

FIGS. 7A through 7D each are diagrams illustrating an embodiment of a reflector employed in a transparent-ultrasonic-sensor-based optical-ultrasonic integrated endoscope apparatus or catheter apparatus according to an embodiment of the present disclosure.

Referring to FIGS. 7A through 7D, various types of reflectors may be used in the transparent-ultrasonic-sensor-based optical-ultrasonic integrated endoscope apparatus or catheter apparatus according to the embodiment of the present disclosure. Representative examples of the reflector include a reflective mirror, a prism, a beam splitter, a dichroic mirror, and the like, and may include any type of reflectors capable of reflecting light or ultrasonic waves.

Figure 8:
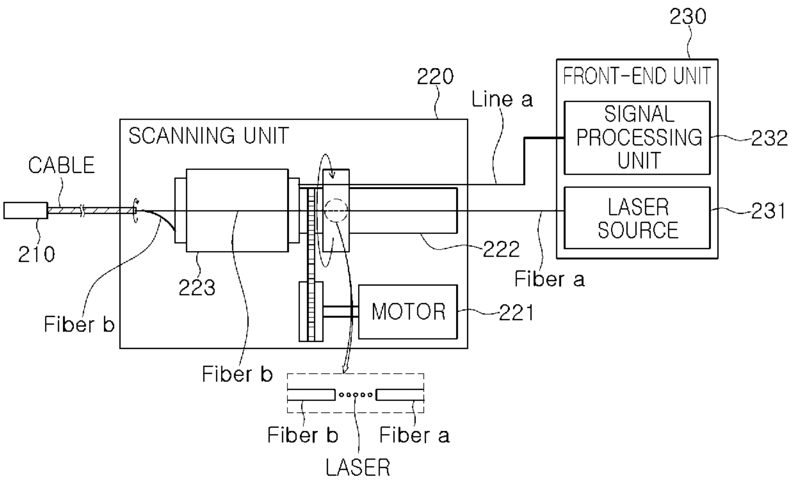
FIG. 8 is a schematic configuration diagram of a transparent-ultrasonic-sensor-based optical-ultrasonic integrated endoscope apparatus or catheter apparatus according to another embodiment of the present disclosure.

FIG. 8 is a schematic configuration diagram of a transparent-ultrasonic-sensor-based optical-ultrasonic integrated endoscope apparatus or catheter apparatus according to another embodiment of the present disclosure.

Referring to FIG. 8, in the case of a side viewing type probe or catheter, a transparent-ultrasonic-sensor-based optical-ultrasonic integrated endoscope apparatus or catheter apparatus 200 according to another embodiment of the present disclosure may include an endoscopic probe or catheter 210, a scanning unit 220, and a front-end unit 230.

The endoscopic probe or catheter 210 may be inserted into a previously set object to acquire an ultrasonic image, photoacoustic image, or the like of an object to be captured.

The scanning unit 220 may control the scanning of the endoscopic probe or the catheter 210 connected through a cable. That is, the scanning unit 220 may rotate the endoscopic probe or catheter 210 by 360E to control a scanning operation of obtaining an ultrasonic image, a photoacoustic image, or the like of an object.

The scanning unit 220 may include a motor 221, an optical fiber rotary joint unit 222 and a slip ring 223.

The motor 221 may provide a torque to rotate the endoscopic probe or catheter 210. The optical fiber rotary joint unit 222 may provide coaxial alignment between an optical fiber cable (fiber b) connected to the endoscopic probe or catheter (210) that rotates according to the torque of the motor 221 and an optical fiber cable (fiber a) connected to and fixed to the front-end unit 230. The fixed optical fiber cable (fiber a) and the optical fiber cable (fiber b) rotated by the motor are spaced apart from each other by approximately several μm, a laser may be transmitted from the fixed optical fiber cable (fiber a) to the rotating optical fiber cable (fiber b) as shown in the dotted line, and the optical fiber rotary joint unit 222 may provide the coaxial alignment between the optical fiber cable (fiber b) that is connected to the endoscopic probe or catheter 210 rotated according to the torque of the motor 221 and rotated and the optical fiber cable (fiber a) that is connected to the front-end unit 230 and fixed to transfer the laser to the optical fiber cable (fiber b) rotated from the optical fiber cable (fiber a) fixed as shown in the dotted line. The slip ring 223 may provide an electrical connection between a signal line (line b) that is connected to the front-end unit 230 and fixed and a signal line (line b) that is connected to the endoscopic probe or catheter 110 rotated by the motor 221 and rotated.

The front-end unit 230 may include a signal processing unit 232 that transmits an ultrasonic signal to the endoscopic probe or catheter 210 through a laser source 231 providing a laser through the optical fiber cable (fiber a) and the signal line (line a), receives and signal-processes the reflected ultrasonic signal, and signal-processes and displays the acquired photoacoustic image or the like.

Figure 9A:
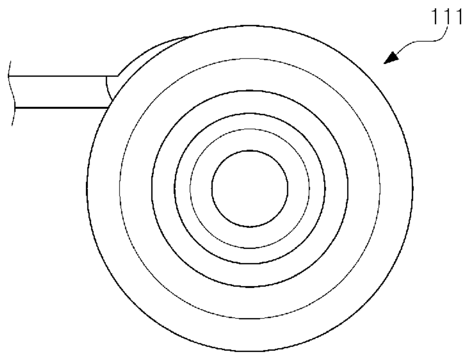
FIG. 9A is a front view of a transparent ultrasonic sensor employed in the transparent-ultrasonic-sensor-based optical-ultrasonic integrated endoscope apparatus or catheter apparatus according to the embodiment of the present disclosure.
Figure 9B:
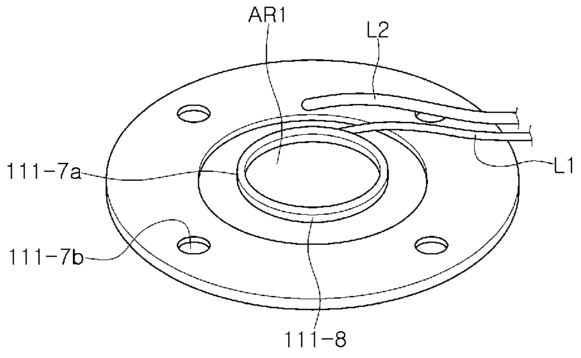
FIG. 9B is a rear view of the transparent ultrasonic sensor according to the embodiment of the present disclosure.
Figure 10:
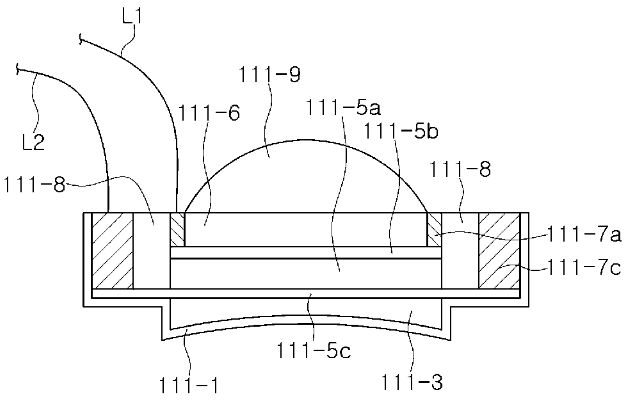
FIG. 10 is a schematic one-way cross-sectional view of the transparent ultrasonic sensor employed in the transparent-ultrasonic-sensor-based optical-ultrasonic integrated endoscope apparatus or catheter apparatus according to the embodiment of the present disclosure.
Figure 11:
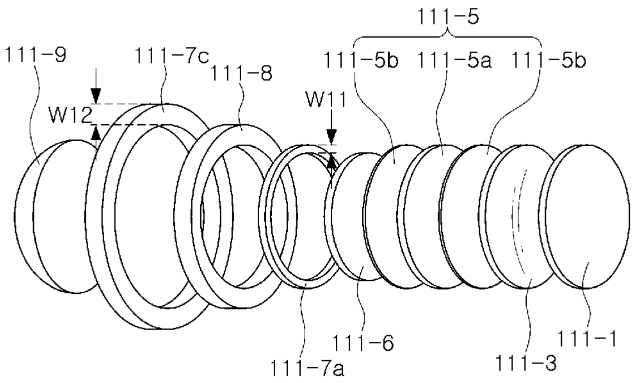
FIG. 11 is a schematic exploded perspective view of the transparent ultrasonic sensor employed in the transparent-ultrasonic-sensor-based optical-ultrasonic integrated endoscope apparatus or catheter apparatus according to the embodiment of the present disclosure.

FIG. 9A is a front view of a transparent ultrasonic sensor employed in the transparent-ultrasonic-sensor-based optical-ultrasonic integrated endoscope apparatus or catheter apparatus according to the embodiment of the present disclosure, and FIG. 9B is a rear view of the transparent ultrasonic sensor according to the embodiment of the present disclosure, FIG. 10 is a schematic one-way cross-sectional view of the transparent ultrasonic sensor employed in the transparent-ultrasonic-sensor-based optical-ultrasonic integrated endoscope apparatus or catheter apparatus according to the embodiment of the present disclosure, and FIG. 11 is a schematic exploded perspective view of the transparent ultrasonic sensor employed in the transparent-ultrasonic-sensor-based optical-ultrasonic integrated endoscope apparatus or catheter apparatus according to the embodiment of the present disclosure.

As illustrated in FIGS. 9A and 9B, the transparent ultrasonic sensor 111 according to the embodiment of the present disclosure has a circular shape having a circular planar shape, but is not limited thereto.

Referring to FIGS. 9A, 9B, and 10, the transparent ultrasonic sensor 111 according to the embodiment of the present disclosure may include, from the right, a protective layer 111-1, a matching unit 111-3 having an acoustic lens located behind the protective layer 111-1, a piezoelectric part 111-5 located behind the matching unit 111-3, first and second housings 111-7*a* and 111-7*b* connected to the piezoelectric part 111-5, a rear layer 111-6 located behind the piezoelectric part 111-5, an insulating part 111-8 located between the first and second housings 111-7*a* and 111-7*b*, and a correcting lens unit 111-9 located behind the second housing 111-7*b*.

The protective layer 111-1 is to physically and electrically protect the transparent ultrasonic sensor 111 and to reduce the difference in acoustic impedance between media to which the ultrasonic signal is to be irradiated, that is, objects. Therefore, the protective layer 111-1 has a protective function and may operate as a matching layer that performs acoustic impedance matching between a liquid (e.g., water) and a living body.

This protective layer 111-1 may be made of a transparent substance. For example, the protective layer 111-1 may contain parylene that is a transparent polymer.

In this example, the acoustic impedance of the protective layer 111-1 may be about 284 Mrayls.

As illustrated in FIGS. 10 and 11, the protective layer 111-1 may be located on a side surface of the second housing 111-7*b* located on the front and side surfaces of the piezoelectric part 111-5 and at an outermost edge of the transparent ultrasonic sensor 111.

Accordingly, the protective layer 111-1 may eventually form the front and side surfaces of the transparent ultrasonic sensor 111.

The matching unit 111-3 located behind the protective layer 111-1 is to reduce the difference in acoustic impedance between the media to which the ultrasonic signal generated from the piezoelectric part 111-5 is to be irradiated and the objects.

That is, when the ultrasonic signals are generated for the operation of the piezoelectric part 111-5, in order to efficiently transmit an ultrasonic signal in water, living tissue, or other media other than air, the acoustic impedance of the medium needs to be adjusted as much as possible, and as a result, loss of ultrasonic energy may be minimized.

Each acoustic lens of the matching unit 111-3 of this example may be a focused type using an acoustic lens capable of adjusting the focus of the light and ultrasonic signal.

As such, since the matching unit 111-3 has a focus control function, the ultrasonic signal reflected from the object and incident on the transparent ultrasonic sensor 111 is accurately focused on the desired location of the piezoelectric part 111-5.

Therefore, by the focus control function of the matching unit 111-3, the focus of the ultrasonic image acquired by the ultrasonic signal output from the piezoelectric part 111-5 may be adjusted to acquire a clear ultrasonic image.

As a result, the clarity of the image obtained by the operation of the transparent ultrasonic sensor 111 is improved, so a clear image of a desired part of the object to which the ultrasonic signal is irradiated may be acquired.

In addition, since the matching unit 111-3 uses an acoustic lens, the curvature of the surface is constant and the transparency of the surface is improved, so the amount of loss of the ultrasonic signal when transmitting or receiving the ultrasonic signal irradiated to or reflected from the object may be reduced.

In addition, if necessary, an additional transmission film or a blocking film may be formed in the matching unit 111-3 to transmit or block only signals of a desired wavelength range.

The acoustic lens provided in the matching unit 111-3 may be made of at least one of transparent glasses, transparent epoxies, and transparent silicones.

Such an acoustic lens may be selected according to the function of the acoustic lens.

For example, in the case where the acoustic lens functions as a matching layer that performs a matching function of acoustic impedance, when the piezoelectric substance provided in the piezoelectric part 111-5 is not in the form of a polymer such as PVDF or PVDF-TrFE, it may be more preferable that the acoustic lens is made of glasses.

That is, when the piezoelectric substance is made of lithium niobite (LNO) or PMN-PT, the acoustic impedance is as high as 30 to 40 Mrayls, but when the piezoelectric substance is made of glasses, the acoustic impedance is low as 10 to 15 Mrayls, and thus, an acoustic impedance value that is easy to match the acoustic impedance is obtained and very good transparency is also obtained. As a result, the acoustic lens may be made of glasses when the piezoelectric substance is not in the form of a polymer.

However, when the matching layer performing the matching function of the acoustic impedance is already manufactured, the acoustic lens may be made of transparent epoxies or transparent silicones.

That is, when the matching layer (about 7 to 20 Mrayls) that performs a matching function between a piezoelectric substance having an acoustic impedance of about 30 to 40 Mrayls and a living tissue or water (i.e., the medium to which the ultrasonic wave is to be irradiated) having an acoustic impedance of about 1 to 2 Mrayls exists in advance, since a separate acoustic impedance matching operation is unnecessary, epoxies or silicones (approximately 1 to 3 Mrayls) having an acoustic impedance similar to that of the living tissue or water are suitable. That is, since the acoustic impedance of epoxies and silicones has acoustic impedance almost similar to that of the living tissue or water, the separate acoustic impedance matching is unnecessary.

In addition, considering a speed of sound and a speed of sound for the material of the acoustic lens, the curvature of the curved surface of the acoustic lens and whether the acoustic lens is concave or convex may be determined.

Figure 12A:
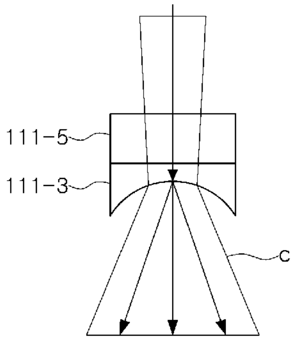
FIGS. 12A and 12B each are exemplary diagrams illustrating paths of light when a plano-concave type of plano-concave acoustic lens and a plano-convex type of plano-convex acoustic lens are used in the transparent ultrasonic sensor employed in the transparent-ultrasonic-sensor-based optical-ultrasonic integrated endoscope apparatus or catheter apparatus according to the embodiment of the present disclosure.

For example, when the acoustic lens is made of glasses, the optical lens may be used. In this case, a speed of light of glasses is faster than that of water, so the acoustic lens may be designed in a concave shape such as a plano-concave (see FIG. 12A).

When the acoustic lens is made of transparent epoxies, a polishing process is performed on the primarily produced acoustic lens to improve transparency as much as possible, thereby finally completing the acoustic lens. As such, even when the acoustic lens is made of epoxies, the speed of light of epoxies is faster than that of water, so the acoustic lenses may also be manufactured in a plano-concave shape.

Figure 12B:
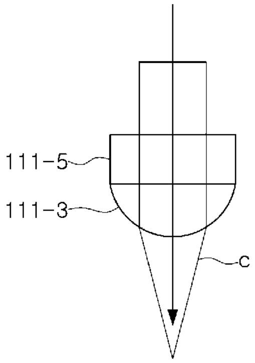

Even when the acoustic lens is made of transparent silicones, as in the case of the epoxies, the separate polishing process should be performed to maximize the completed acoustic lens as much as possible. In this case, since the speed of light of silicones is slower than that of water, the acoustic lens may be manufactured in a convex shape such as a plano-convex shape, unlike the case of glasses and epoxies (see FIG. 12B). As such, when the acoustic lens is manufactured in the plano-convex shape, the acoustic lens may have a function of converging light.

As illustrated in FIGS. 10 and 11, the piezoelectric part 111-5 may include the piezoelectric layer 111-5*a* and the first and second electrode layers 111-5*b* and 111-5*c* located on the rear and front surfaces of the piezoelectric layer 111-5*a*, respectively.

The piezoelectric layer 111-5*a* is a layer in which a piezoelectric effect and a reverse piezoelectric effect occur, and as described above, may contain a piezoelectric substance that is at least one of lithium niobite (LNO), PMN-PT, PVDF, and PVDF-TrFE.

The electromechanical coupling coefficient of LNO is about 0.49, which is very high, so the electromechanical energy conversion efficiency is very good.

In addition, since the LNO has a low dielectric permittivity, when the piezoelectric layer 111-5*a* is made of LNO, the use of the transparent ultrasonic sensor may be suitable for a large aperture single element transducer.

In addition, since the LNO has a high Curie temperature and may withstand high temperature, the transparent ultrasonic sensor 111 having good heat resistance may be developed.

In addition, when the piezoelectric layer 111-5*a* is made of LNO, a single element ultrasonic sensor having a center frequency of 10 to 400 MHz may be easily developed.

When the piezoelectric layer 111-5*a* contains PMN-PT, since the piezoelectric performance (d33~1500-2800 pC/N) and electromechanical coupling coefficient (k>09) of PMN-PT are very high, the performance of the transparent ultrasonic sensor 111 may be improved.

Unlike the LNO, the PMN-PT has a high dielectric permittivity, so the transparent ultrasonic sensor 111 suitable for a small aperture single or array ultrasonic transducer may be developed.

In addition, when the piezoelectric layer 111-5*a* contains at least one of PVDF and PVDF-TrFE, the piezoelectric layer 111-5*a* may have the following characteristics.

The PVDF and PVDF-TrFE have a polymer film form and may be used to manufacture a flexible and stretchable piezoelectric layer 111-5*a*, so it is possible to reduce the thickness of the piezoelectric layer 111-5*a* and to manufacture the transparent ultrasonic sensor 111 for a signal of a high frequency band of about 100 MHz as much as the reduced thickness.

In addition, the PVDF and PVDF-TrFE may have relatively low electromechanical coupling coefficients and high receiving constants and have a wider bandwidth than other piezoelectric substances, and may be easily used to manufacture a single element or all array type elements.

Here, a single element (e.g., a single ultrasonic transducer) may mean an ultrasonic transducer in which the number of all components including a piezoelectric substance is one. In addition, the array type element (e.g., array ultrasonic transducer) may be an ultrasonic transducer having a plurality (n) of all components including a piezoelectric substance, and may generally be configured in a form mainly used in hospitals. In this case, the shape may be a linear shape, a convex shape, a 2D matrix, or the like.

In the case of this example, similar to the PMN-PT, it may be possible to manufacture both single or array ultrasonic transducers with a small aperture.

The substance characteristics of the piezoelectric layer 111-5*a* may be summarized in the table below.

TABLE

| | LNO | PMN-PT | PVDF&PVDF-TrFE |
|---|---|---|---|
| Size | Large | Small | Medium |
| Bandwidth Size | Medium | Medium | Broad |
| Available Frequency Range | 1~400 MHz | 1~100 MHz | 1 KHz~100 MHz |
| Signal Transmission Performance | Good | Good | Bad |
| Signal Reception Performance | Good | Good | Good |
| Electromechanical Coupling Coefficient | Medium | Good | Bad |

The first and second electrode layers 111-5*b* and 111-5*c* located on the front and rear surfaces of the piezoelectric layer 111-5*a*, respectively, may receive a (+) driving signal and a (−) driving signal from a driving signal generator (not illustrated), respectively, and exerts a reverse piezoelectric effect on the piezoelectric layer 111-5*a* so that the ultrasonic signal may be transmitted toward the object 200, and conversely, may receive an electrical signal generated by the piezoelectric effect of the piezoelectric layer 111-5*a* by the ultrasonic signal reflected from an object and output the received electrical signal to the outside.

As described above, the first and second electrode layers 111-5*b* and 111-5*c* may be made of a transparent conductive substance, and may include, for example, at least one of AgNW (silver nanowire), ITO, carbon nanotube, and graphene.

As illustrated in FIG. 10, for easy coupling with the first housing 111-7*a* and the second housing 111-7*b*, the size of the first electrode layer 111-5*b* and the size of the second electrode layer 111-5*c* may be different from each other.

Therefore, as illustrated in FIG. 10, in the first and second electrode layers 111-5*b* and 111-5*c* having a circular planar shape, the diameter of the second electrode layer 111-5*c* is different from that of the first electrode layer, and a portion (e.g., edge portion) of the second electrode layer 111-5*c* may protrude from the edge portion of the first electrode layer 111-5*b* to the outside.

When the electrical signal (e.g., pulse signal) is applied to the piezoelectric substance, the piezoelectric substance (i.e., the piezoelectric layer 111-5*a*) vibrates back and forth to generate an ultrasonic signal. The ultrasonic signal is generated not only on the front surface of the piezoelectric layer 111-5*a* facing the object, but also on the rear surface that is opposite to the front surface.

In this case, since the ultrasonic signal generated on the rear surface is not directed to the object, the ultrasonic signal generated on the rear surface acts as a noise signal.

In addition, a portion of the ultrasonic signal reflected from the object and returned may pass through the matching unit 111-5 and be output toward the correcting lens unit 111-9.

Therefore, the rear layer 111-6 may be located on the rear surface of the piezoelectric part 111-5 to damp the ultrasonic signal generated from the rear surface of the piezoelectric part 111-5 and to damp the ultrasonic signal reflected from the object.

As such, since the rear layer 111-6 is located on the rear surface (that is, the surface opposite to the front surface of the piezoelectric part 111-5 on which the reflected ultrasonic signal is incident) of the piezoelectric part 111-5, the ultrasonic signal does not pass through the rear surface of the piezoelectric part 111-5.

In this way, it is possible to prevent unnecessary signal interference by an ultrasonic signal passing through the rear surface of the piezoelectric part 111-5, and to prevent the loss of the ultrasonic signal reflected to the piezoelectric part 111-5 to reduce a ring-down signal, to thereby reduce the ring-down phenomenon.

The ring-down is a phenomenon in which unnecessary signals are elongated along a time axis, which is a factor that adversely affects image generation.

Accordingly, the rear layer 111-6 may be properly manufactured by adjusting at least one of acoustic impedance and thickness in order to reduce such a ring-down phenomenon.

When the rear layer 111-6 is made of a substance with high acoustic impedance, the ring-down phenomenon is reduced, and the reduction of the ring-down phenomenon on the time axis is similar to the meaning that a bandwidth is widened in a frequency domain. However, when transmitting/receiving the ultrasonic signal instead, the size of the entire ultrasonic signal may also be damped by the rear layer 111-6.

Conversely, when the rear layer 111-6 is made of a substance having relatively low acoustic impedance, the ring-down phenomenon is not significantly reduced and the bandwidth is reduced, but the amount of transmission/reception of ultrasonic signal may be increased.

The rear layer 111-6 may also be made of a transparent non-conductive substance, and may be made of, for example, transparent epoxies (e.g., Epotek301) or transparent glasses.

When the rear layer 111-6 is made of Epotek301, and has the acoustic impedance as low as 31 Mrayls, low signal damping is achieved so the transparent ultrasonic sensor 111 may obtain a relatively high signal.

In addition, Epotek301 has very high transparency, such as having transparency of about 95% or more at a wavelength of 380 nm to 2000 nm, and it is easy to manufacture the rear layer 111-6 because it is cured at room temperature.

When the rear layer 111-6 is made of glass, the transparency and flatness are high, and a separate curing process is unnecessary.

When glass has an acoustic impedance of about 13 Mrayls, the pulse length is reduced due to the high signal damping in the rear layer 111-6 to reduce the ring-down effect, but the effect of increasing the frequency bandwidth of the transparent ultrasonic sensor 111 may be exerted.

The rear layer 111-6 may be omitted if necessary.

As described above, the first housing 111-7*a* and the second housing 111-7*b* are connected to the first electrode layer 111-5*b* and the second electrode layer 111-5*c*, respectively. Accordingly, the first housing 111-7*a* and the second housing 111-7*b* may be made of a transparent conductive substance containing a conductive substance (e.g., copper) through which an electrical signal is transmitted.

Therefore, as illustrated in FIG. 3, the first housing 111-7*a* may receive the corresponding signal through a first signal line L1 and transmit the received signal to the first electrode layer 111-5*b*, and conversely, output the signal applied from the first electrode layer 111-5*b* to the first signal line L1.

The second housing 111-7*b* may also receive the corresponding signal through a second signal line L2, which is a separate signal line from the first signal line L1, and transmit the received signal to the second electrode layer 111-5*c*, and conversely, output the signal applied from the second electrode layer 111-5*c* to the second signal line L2.

In this example, the signal input to the first signal line L1 may be a pulse signal, and the signal introduced into the second signal line L2 may be a ground signal or a shield signal (−), so the first housing 111-7*a* may transmit the pulse signal to the first electrode layer 111-5*b* and the second housing 111-7*b* may transmit the ground signal to the second electrode layer 111-5*c*.

As illustrated in FIG. 4, the first housing 111-7*a* and the second housing 111-7*b* have a ring shape, and may be located in contact with edge portions of the corresponding electrode layers 111-5*b* and 111-5*c*, that is, a circular side surface.

That is, the first electrode layer 111-5*b* and the second electrode layer 111-5*c* may be inserted and mounted into the empty space located inside the first housing 111-7*a* and the second housing 111-7*b*.

Therefore, as illustrated in FIG. 9, the first housing 111-7*a* and the second housing 111-7*b* are located so that the transparent ultrasonic sensor 111 encloses the actual active area AR1, to thereby minimize a reduction in an active area AR1 by the first and second housings 111-7*a* and 111-7*b*, substantially the first housing 111-7*a*.

As such, since the first housing 111-7*a* and the second housing 111-7*b* serve to transmit electrical signals to the corresponding electrode layers 111-5*b* and 111-5*c*, the first housing 111-7*a* and the second housing 111-7*b* may contain a substance with good conductivity.

Since the first housing 111-7*a* is located at the edge portion (i.e., corner portion) of the first electrode layer 111-5*a* located on the entire rear surface of the piezoelectric layer 111-5*a* where light is received, the first housing 111-7*a* preferably has a width W11 as thin as possible, and may have a thickness as thick as possible to minimize a signal loss rate due to wiring resistance or the like.

Since the second housing 111-7*b* is coupled with the second electrode layer 111-5*c* having a diameter larger than that of the first electrode layer 111-5*b* as illustrated in FIGS. 9 and 10, the second housing 111-7*b* has a larger diameter than that of the first housing 111-7*a*.

In addition, since the second housing 111-7*b* serves to protect the transparent ultrasonic sensor 111 from the outside more than the first housing 111-7*a*, the second housing 111-7*b* may have the width and thickness larger that those of the first housing 111-7*a*.

Therefore, as illustrated in FIG. 10, the first electrode layer 111-5*b* and the first housing 111-7*a* may be located in the second housing 111-7*b*.

In addition, as described above, the outer side surface of the second housing 111-7*b* exposed to the outside is covered with the protective layer 111-1, so the noise signal is prevented from entering the transparent ultrasonic sensor 111 through the second housing 111-7*b*.

As illustrated in FIGS. 10 and 11, the second housing 111-7*b* does not affect a light receiving area of the piezoelectric layer 111-5*a*, so the size may be increased if necessary.

In addition, the desired optical component may be coupled to the second housing 111-7*b* by forming a screw 111-7*b*1, a connector, or the like on the second housing 111-7*b*. In this case, the second housing 111-7*b* may function as a coupling part for coupling with other components.

The insulating part 111-8 is located between the first housing 111-7*a* and the second housing 111-7*b* that transmit the corresponding electrical signals to the corresponding electrode layers 111-5*b* and 111-5*c* to be in contact with the first housing 111-7*a* and the second housing 111-7*b* to insulate the first housing 111-7*a* and the second housing 111-7*b*, to thereby prevent electrical short-circuit or short, and may serve to fix the locations of the first housing 111-7*a* and the second housing 111-7*b*.

Figure 13A:
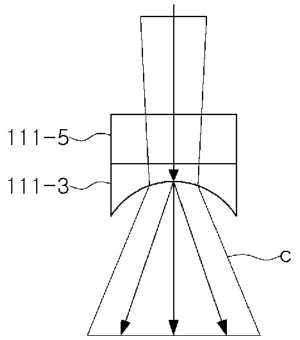
FIGS. 13A and 13B each are exemplary diagrams illustrating an example illustrating paths of light when a correcting lens is used and when a correcting lens is not used in the transparent ultrasonic sensor employed in the transparent-ultrasonic-sensor-based optical-ultrasonic integrated endoscope apparatus or catheter apparatus according to the embodiment of the present disclosure.

The insulating part 111-8 may be made of a transparent insulating substance such as non-conductive epoxy. As an example of the matching unit 111-3, when the plano-concave acoustic lens is used, the focus of the light and ultrasonic signals reflected from an object and incident is adjusted by the acoustic lens of the matching unit 111-3. However, after the light and ultrasonic signal pass through the matching unit 111-3, the light spreading phenomenon may occur (see FIG. 13A).

Figure 13B:
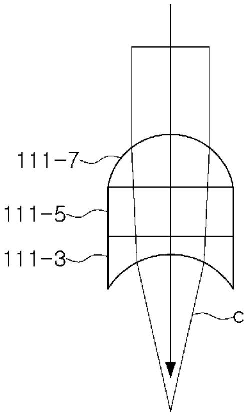

Therefore, the correcting lens part 111-9, which has the plano-convex shape opposite to the shape of the acoustic lens used in the matching unit 111-3, may be located in front of the rear layer 111-7, and compensate for the refraction phenomenon of light to prevent the light spreading phenomenon (see FIG. 13B).

In this case, the curvature of the correcting lens unit 111-9 may be selectively used depending on where the light is finally located.

As such, the correcting lens unit 111-9 may affect only the focus of light regardless of the focus of the ultrasonic signal, but the acoustic lens of the matching unit 111-3 may affect both the focus of the ultrasonic signal and the focus of light.

The correcting lens unit 111-9 may be omitted if necessary, and the focal length of light may be adjusted by changing the correcting lens unit 111-9.

In addition, the correcting lens unit 111-9 may have a confocal function of simultaneously adjusting the focus of the reflected and received ultrasonic signal and the focus of light. However, when the correcting lens unit 111-9 has the confocal function, the correcting lens unit 111-9 needs to be designed in consideration of the shape of light before passing through the transparent ultrasonic sensor 111.

In this example, the correcting lens unit 111-9 includes a single lens, but is not limited thereto, and may include a plurality of lenses by additionally including a lens for aberration correction in addition to a single lens such as the plano-convex lens.

The characteristics of the transparent ultrasonic sensor 111 of this example in which all components (e.g., 111-1 to 111-6, 111-9) located in the active area AR1 of the transparent ultrasonic sensor 111 having this structure are made of a transparent material through which light is transmitted may be as follows.

First, since the optical impedance matching, that is, the matching is performed by the operation of the matching unit 111-3, the reliability of the signal output from the transparent ultrasonic sensor 111 may be improved.

In addition, due to the use of the acoustic lens equipped with the focus control function used in the matching unit 111-3, the focus of the light reflected by the object and the ultrasonic signal may be adjusted, so the light and ultrasonic signal may be focused on the exact desired location of the piezoelectric part 111-5. As a result, the clarity of the ultrasonic image acquired by the signal output from the transparent ultrasonic sensor 111 is greatly improved, so it is possible to grasp the exact shape of the detected object as well as whether or not the object exists.

In addition, as described above, since the components (e.g., 11-16, 19) constituting the transparent ultrasonic sensor 111 are all made of transparent materials such as transparent glasses, transparent epoxies, and transparent silicones, the light output from the optical fiber laser unit 112 may directly pass through the transparent ultrasonic sensor 111 and be irradiated toward the corresponding object.

As a result, the arrangement of the optical system including the transparent ultrasonic sensor 111 may be free, and the utilization of the space in which the optical system is installed may be improved.

In addition, the correcting lens unit 111-9 may be selectively used according to user requirements, and the focal length of light may be adjusted by changing the correcting lens unit 111-9.

In addition, when the plano-concave optical lens coated to 400 to 1000 nm is used as the acoustic lens, light transmits well at 400 to 1000 nm, so the clarity of an ultrasonic image may be improved.

When the plano-concave optical lens is used as the acoustic lens 111-3, the light spreading shape by the acoustic lens occurs, but the light spreading shape by the correcting lens part 111-9 is supplemented and the focus of light may be adjusted to a desired point. As such, the range of selection of the acoustic lens may be widened by using the compensating lens.

The shape of light is maintained by the focus adjustment by the acoustic lens 111-3 and the correcting lens unit 111-9, and as a result, fine focus may be maintained, so the high-resolution optical image (e.g., photoacoustic image or optical coherence tomography images) may be obtained.

In addition, the first and second signal lines L1 and L2 may be connected to the first and second housings **111-7*a* and 111-7*b* constituting the housing of the transparent ultrasonic sensor 111, respectively, to apply an electrical signal to the first and second electrodes 111-5*b* and 111-5*c*, so it is possible to easily connect the signal lines L1 and L2**.

Furthermore, by forming a thread **111-7*b*1 or the like in the second housing 111-7*b* which is an outer housing, it is possible to facilitate connection or coupling with other optical elements. In this way, since the necessary optical elements are coupled to the second housing 111-7*b* located in a portion completely unrelated to the path of light emitted from the optical module 100, the light is normally incident on the piezoelectric part 111-5 of the transparent ultrasonic sensor 111 without loss and passes through the center of the transparent ultrasonic sensor 111** in a normal direction, so the alignment of the light and the ultrasonic signal may be easily achieved.

Here, the meaning of vertical may mean that light travels in a direction perpendicular to the incident surface of the transparent ultrasonic sensor (e.g., transparent ultrasonic transducer).

In this way, when light is incident vertically on the ultrasonic sensor, the focus position of the light and ultrasonic signal may be precisely matched, so the clarity of the image acquired from the transparent ultrasonic sensor may be further improved.

As described above, the matching layer may be present to minimize ultrasonic energy loss in the medium due to the difference in acoustic impedance between air and the medium.

One or more matching layers may be present.

In Comparative Example, such a matching layer may be formed as follows.

When the medium of the ultrasonic signal is water or biological tissue (15 Mrayls), in the case where the piezoelectric layer is LNO (345 Mrayls) or PMN-PT (371 Mrayls), the acoustic impedance matching is required for maximum transmission/reception efficiency of ultrasonic energy. In this case, one or more matching layers may be required, with substances ranging from 371 Mrayls to 15 Mrayls.

In this case, when a specific matching layer is generated using KLM simulation tools (PiezoCAD, PZFLEX, etc.), it is necessary to find the substance of the appropriate matching layer by checking the waveform of the ultrasonic signal transmitted from water or living tissue through simulation, and since the thickness of the generated matching layer also affects the ultrasonic waveform, the thickness also greatly affects the waveform, and thus, it is necessary to find an appropriate thickness by adjusting the thickness of the matching layer. Theoretically, the thickness of the minimum loss of wave energy is the minimum loss at the thickness of $\lambda/4$ desired by the wave equation ($c=\lambda*f$, c: speed of sound of about 1480 m/s, $\lambda$: wavelength, f: desired center frequency).

In the conventional ultrasonic sensor, a first matching layer is often formed with a mixture of silver powder and epoxy (79 Mrayls). In this case, the acoustic impedance may be adjusted according to the mixing ratio of the silver powder and the epoxy, and for example, silver powder: epoxy=3:125.

Next, the second matching layer may be formed through parylene (28 Mrayls) coating.

When the piezoelectric layer is PVDF or PVDF-TrFE (about 4 Mrayls), one matching layer may be generated using only the parylene coating. Here, the matching layer formed by the parylene coating may serve not only as a matching layer but also as protection and insulation from the outside.

However, in the case of the transparent ultrasonic sensor 111 according to the present example, since the components (e.g., 11 to 16, 19) located in the active area AR1 are transparent, in the case of the LNO or PMN-PT constituting the piezoelectric layer, the matching layer 111-3 may be formed using glass. In this case, depending on the raw material of glass (e.g., borosilicate glass=13 Mrayls, Crown glass=142 Mrayls, Quartz=145 Mrayls, plate glass=107

Mrayls, sodalime glass=13 Mrayls), it is slightly different, so it is possible to select and use the desired glass appropriately.

Then, the second matching layer (e.g., 2 to 6 Mrayls) may be generated using transparent epoxies or silicones (e.g., PDMS), and the third matching layer may be generated using the parylene coating. In this case, the generation of the second matching layer may be omitted, and the second matching layer (e.g., 11) may be formed on the first matching layer (e.g., 13) using the parylene coating. Even in this case, the desired matching layer may be generated using a simulation waveform resulting from the KLM simulation.

In the transparent ultrasonic sensor 111 according to this example, as an example, an engineering lens made of borosilicate is used as a first matching layer, and the second matching layer is formed on the first matching layer through the parylene coating to perform the acoustic impedance matching and the protection and signal insulation from the outside.

As described above, this optical lens may perform not only the function of the acoustic impedance matching, but also the role of condensing, that is, focusing, the ultrasonic signal generated from the piezoelectric layer.

Since the transparent ultrasonic sensor 111 is mainly used for image acquisition, the focusing of the ultrasonic signal is a factor that greatly affects high resolution and high sensitivity.

Figure 14:
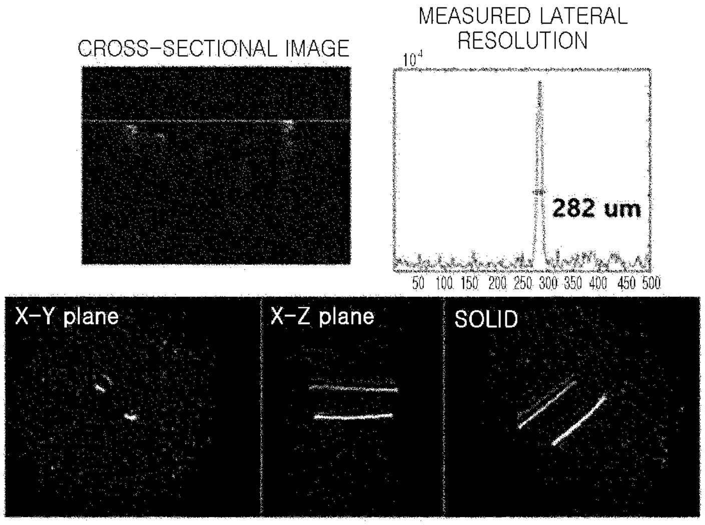
FIGS. 14 and 15 are diagrams illustrating photoacoustic image results acquired by the transparent-ultrasonic-sensor-based optical-ultrasonic integrated catheter apparatus according to the embodiment of the present disclosure.
Figure 15:
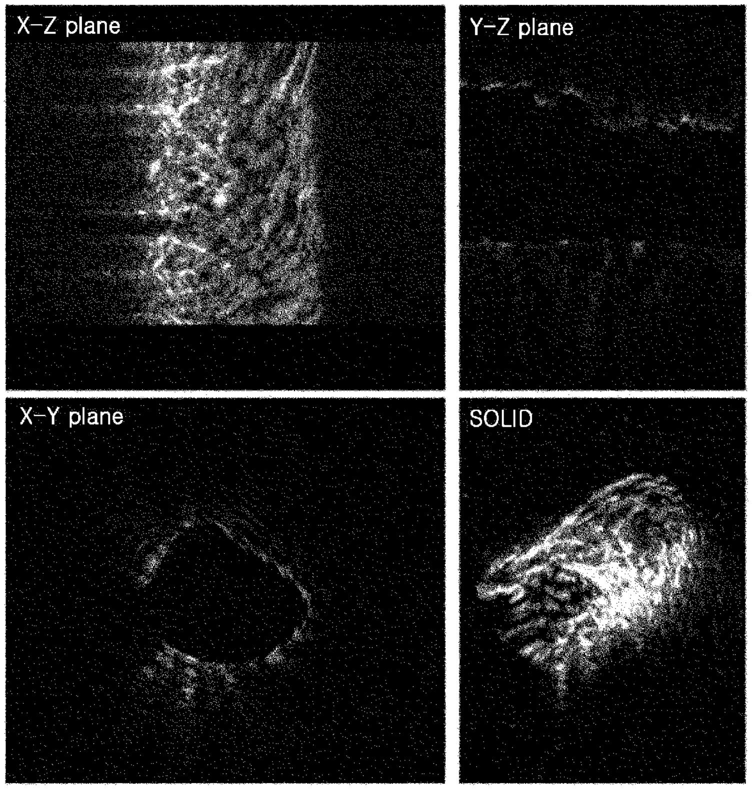

FIGS. 14 and 15 are diagrams illustrating photoacoustic image results acquired by the transparent-ultrasonic-sensor-based optical-ultrasonic integrated catheter apparatus according to the embodiment of the present disclosure.

Referring to FIG. 14, it was experimented whether the photoacoustic image may be acquired by attaching hair to a 4.0 mm hole and inserting the catheter of the transparent-ultrasonic-sensor-based optical-ultrasonic integrated catheter apparatus according to the embodiment of the present disclosure into the 4.0 mm hole. As illustrated, 3D data acquired by moving and rotating the catheter forward and backward is expressed as a cross-sectional image, an X-Y plane, an X-Y plane, and the like. The lateral resolution measured with hair was confirmed to be 282 μm.

Referring to FIG. 15, it was experimented whether the photoacoustic image may be acquired by rolling and attaching a leaf skeleton phantom to a 4.5 mm hole and inserting the catheter of the transparent-ultrasonic-sensor-based optical-ultrasonic integrated catheter apparatus according to the embodiment of the present disclosure into the 4.0 mm hole. As illustrated, 3D data acquired by moving and rotating the catheter forward and backward is expressed as an X-Z plane, an X-Y plane, an X-Y plane, and the like.

In the conventional ultrasonic-photoacoustic endoscope and intravascular catheter using the opaque ultrasonic sensor, it is very difficult to position both the optical fiber and the ultrasonic sensor within a limited space, and it is very difficult to synchronize the laser field of view and the ultrasonic field of view at the same time. In addition, various methods such as OCT, fluorescence, and infrared may be used to accurately diagnose intravascular diseases (what is observed is different for each system), but it is very difficult to develop a system with a limited size. As described above, when the transparent ultrasonic sensor according to the present disclosure is used, the limited space may be maximally utilized and it is easy to combine various optical modules. In addition, when using the existing ultrasonic sensor, there may be restrictions on the use of the optical system existing on the optical path, but when using the transparent ultrasonic sensor, there is freedom in using the optical system at any location. In addition, the transparent ultrasonic sensor may provide comprehensive information by coupling with various types of general optical imaging equipment. In particular, as for the endoscope or catheter, many studies have already been conducted to combine the ultrasonic and optical images (photoacoustic/OCT/fluorescence/NIRS/NIRF images, etc.). However, since the imaging equipment needs to be directly inserted into a tube or blood vessel in a body, the size of the imaging equipment is very limited. The combination of the transparent ultrasonic sensor and the optical imaging equipment is optimized to minimize the size.

The present disclosure described above is not limited by the above-described embodiments and the accompanying drawings, but is limited by the claims described below, and it can be readily understood by those skilled in the art that the configuration of the present disclosure may variously be changed and modified within the scope without departing from the technical spirit of the present disclosure.

The invention claimed is:

1. A transparent-ultrasonic-sensor-based optical-ultrasonic integrated endoscopic probe, comprising:
- an optical fiber laser unit emitting light;
- a transparent ultrasonic sensor arranged between an object to be measured and the optical fiber laser unit to transmit, therethrough, the light emitted from the optical fiber laser unit, coaxially aligned with the light emitted from the optical fiber laser unit, radiating ultrasonic waves at the object, and receiving reflected ultrasonic waves;
- a camera acquiring an image of the object through the transparent ultrasonic sensor; and
- an optical lens arranged between the transparent ultrasonic sensor and the optical fiber laser unit, and adjusting characteristics of light from the optical fiber laser unit, wherein the transparent ultrasonic sensor includes:
- a matching unit performing optical impedance matching and made of a transparent material;
- a piezoelectric unit located behind the matching unit, radiating the ultrasonic waves and made of the transparent material; and
- a correcting lens unit located behind the piezoelectric unit, adjusting a focus of light passing through the matching unit and made of a transparent material.

2. The transparent-ultrasonic-sensor-based optical-ultrasonic integrated endoscopic probe of claim 1, further comprising:
- a suction unit sucking a pre-set substance;
- a plurality of forceps holes performing a pre-set medical function; and
- at least one of water nozzles spraying water.

3. The transparent-ultrasonic-sensor-based optical-ultrasonic integrated endoscopic probe of claim 1, further comprising:
- a reflector changing a path of light from the optical fiber laser unit to a preset angle.

4. The transparent-ultrasonic-sensor-based optical-ultrasonic integrated endoscopic probe of claim 1, wherein the optical lens is provided in plurality.

5. The transparent-ultrasonic-sensor-based optical-ultrasonic integrated endoscopic probe of claim 1, wherein the transparent ultrasonic sensor includes:
- a first electrode layer and a second electrode layer each made of a transparent conductive material located on back and front surfaces of the piezoelectric unit;
- a first housing connected to the first electrode layer; and
- a second housing connected to the second electrode layer.

6. The transparent-ultrasonic-sensor-based optical-ultrasonic integrated endoscopic probe of claim 5, further comprising:

an insulating part located between the first housing and made of a transparent insulating substance.

7. The transparent-ultrasonic-sensor-based optical-ultrasonic integrated endoscopic probe of claim 5, further comprising:

a protective layer located in front of the matching unit and performing acoustic impedance matching.

* * * * *